(12) United States Patent
Kwon et al.

(10) Patent No.: US 9,181,278 B2
(45) Date of Patent: Nov. 10, 2015

(54) METHOD OF PREPARING CARBON NANOTUBE COMPOSITE SURFACE HAVING METAL PARTICLES

(71) Applicant: ELECTRONICS AND TELECOMMUNICATIONS RESEARCH INSTITUTE, Daejeon (KR)

(72) Inventors: Jong Hwa Kwon, Daejeon (KR); Ho Gyu Yoon, Seoul (KR); Kwang Se Lee, Daejeon (KR)

(73) Assignee: ELECTRONICS AND TELECOMMUNICATIONS RESEARCH INSTITUTE, Daejeon (KR)

(*) Notice: Subject to any disclaimer, the term of this patent is extended or adjusted under 35 U.S.C. 154(b) by 0 days.

(21) Appl. No.: 14/322,533

(22) Filed: Jul. 2, 2014

(65) Prior Publication Data

US 2014/0316152 A1    Oct. 23, 2014

Related U.S. Application Data

(62) Division of application No. 12/966,214, filed on Dec. 13, 2010, now abandoned.

(30) Foreign Application Priority Data

Dec. 21, 2009  (KR) .................. 10-2009-0128444

(51) Int. Cl.
| | |
|---|---|
| *C07F 7/08* | (2006.01) |
| *C07F 1/00* | (2006.01) |
| *B82Y 30/00* | (2011.01) |
| *B82Y 40/00* | (2011.01) |
| *C09D 183/08* | (2006.01) |
| *C08G 77/26* | (2006.01) |

(52) U.S. Cl.
CPC ............. *C07F 1/005* (2013.01); *B82Y 30/00* (2013.01); *B82Y 40/00* (2013.01); *C07F 7/0854* (2013.01); *C09D 183/08* (2013.01); *C07B 2200/11* (2013.01); *C08G 77/26* (2013.01)

(58) Field of Classification Search
CPC ..................................... C07F 7/08; C07F 7/18
USPC .................................. 556/12, 400, 413, 425
See application file for complete search history.

(56) References Cited

FOREIGN PATENT DOCUMENTS

| JP | 2009-102179 | 5/2009 |
|---|---|---|
| JP | 2009102179 A * | 5/2009 |
| KR | 10-2005-0037877 | 4/2005 |
| KR | 10-2008-0050735 | 6/2008 |
| KR | 10-2008-0099368 | 11/2008 |
| KR | 10-2009-0009419 | 1/2009 |
| KR | 10-2009-0029409 | 3/2009 |
| KR | 10-2009-0037564 | 4/2009 |
| KR | 10-2009-0083039 | 8/2009 |

OTHER PUBLICATIONS

X. Pei et al., "Preparation and characterization of carbon nanotube-polymer/Ag hybrid nanocomposites via surface RAFT polymerization", Journal of the Physical Chemistry C, vol. 111, pp. 2947-2952, Jan. 27, 2007.
Y. Oh et al., "Silver-plated carbon nanotubes for silver/conducting polymer composites", Nanotechnology, vol. 19, pp. 1-7, Nov. 19, 2008.
S. S. Bale et al., "Protein-directed formation of silver nanocomparticles on carbon nanotubes", Advanced materials, vol. 19, pp. 3167-3170, Oct. 17, 2007.
K. Dai et al., "Synthesis of silver nanoparticles on functional multi-walled carbon nanotubes", Materials science and engineering A, vol. 465, pp. 283, Sep. 15, 2007.
Lee et al., "Self-Organized Grafting of Carbon Nanotubes by End-Functionalized Polymers", Macromolecular Research, vol. 16, No. 3, Apr. 30, 2008, pp. 261-266.
Peng et al., "Sidewall Carboxylic Acid Fucntionalization of Single-Walled Carbon Nanotubes", J. Am. Chem. Soc. 2, 125, Nov. 15, 2003, pp. 15174-15182.
Office Action (Restriction) mailed Jan. 25, 2013 in co-pending U.S. Appl. No. 12/966,214.
Office Action mailed Nov. 7, 2013 in co-pending U.S. Appl. No. 12/966,214.
Final Office Action mailed Apr. 1, 2014 in co-pending U.S. Appl. No. 12/966,214.
U.S. Appl. No. 12/966,214, filed Dec. 13, 2010, Jong Hwa Kwon et al., Electronics and Telecommunications Research Institute.

* cited by examiner

Primary Examiner — Sudhakar Katakam
(74) Attorney, Agent, or Firm — Staas & Halsey LLP (57) ABSTRACT

A method of preparing a carbon nanotube composite with metal particles on a surface thereof, including: introducing an acylhalide group to the surface, causing a reaction of the acylhalide group with an amine group of a polysiloxane to bond the polysiloxane to the surface by the amide groups, and introducing metal particles to other functional groups of the polysiloxane to bond the metal particles to the surface of the carbon nanotube composite.

5 Claims, 6 Drawing Sheets

METHOD OF PREPARING CARBON NANOTUBE COMPOSITE SURFACE HAVING METAL PARTICLES

CROSS-REFERENCE TO RELATED APPLICATIONS

This application is a Divisional of U.S. application Ser. No. 12/966,214 filed Dec. 13, 2010, and claims the benefit of priority from Korean Patent Application No. 10-2009-0128444 filed in the Korean Intellectual Property Office on Dec. 21, 2009, the disclosures of which are incorporated herein by reference in its entirety.

BACKGROUND OF THE INVENTION

1. Field of the Invention

The present invention relates to a carbon nanotube (CNT) composite and a preparation method of the same, and particularly to a CNT composite on which metal particles can be uniformly fixed, that has improved mechanical and electrical properties, and that can be applied to various industrial fields, and a preparation method of the same.

2. Description of the Related Art

Since the discovery of carbon nanotubes (CNT) was reported by Iijima in 1991, numerous studies regarding CNT as a nano-material have been undertaken, and remarkable improvements in the physical and mechanical properties of the CNT have been reported by many researchers.

Recently, interest in the CNT has increased because the CNT is expected to contribute to future nano-engineering fields when it is used as a reacting template for growing nanotubes or nanorods of other materials. Particularly, applied research on nano-electron device technologies such as a CNT memory and a logic device that will overcome the limitations of the present semiconductor technology, a field emission emitter and a display application technology using its superior field emission property, application technologies of a fuel cell and a lithium ion battery using its large surface area, a composite for an electromagnetic shield and a highly sensitive material, a highly sensitive nano-sensor, and the like are being carried out at home and abroad.

Furthermore, research on CNT-nanoparticle composites of which the nanoparticles are bonded to the CNT is actively being undertaken. According to the research, the CNT-nanoparticle composite can be applied to a catalyst, a chemical sensor, or a nano-sized electromagnetic device, because it is possible to apply the properties of the nanoparticles as well as the properties of the CNT itself. For such applications, various technologies for fixing the nanoparticles to the CNT while maintaining the inherent properties of the CNT and the nanoparticles are being developed.

Particularly, since the CNT-metal nanoparticle composite can be utilized as many forms of electronic materials, various methods for fixing the metal nanoparticles to the CNT have been suggested. For example, a preparation method of the composite by physically mixing the CNT and metals has been suggested, but it has a disadvantage in that it is difficult to apply the composite as an electronic material, because the metals are not properly bonded to the CNT in the composite, or are not dispersed uniformly and are agglomerated together. Accordingly, a method of chemically bonding the metal to the CNT has been suggested, but it has a problem that the metal nanoparticles are not uniformly fixed to the CNT and the size of the metal particles fixed thereto is not uniform.

SUMMARY OF THE INVENTION

An aspect of the present invention is to provide a CNT composite that can fix metal particles uniformly and highly densely on the surface of CNT, has improved mechanical and electrical properties, and can be applied to various industrial fields.

Another aspect of the present invention is to provide a preparation method of the CNT composite.

The present invention provides a CNT composite of which one or more specific functional groups are bonded to surface of a CNT.

The present invention also provides a preparation method of the CNT composite including the steps of introducing an acylhalide group to the surface of a CNT, and causing a reaction of the acylhalide group with a polysiloxane having amine groups so as to prepare a CNT composite of which the polysiloxane is bonded to the surface by the medium of an amide group.

DETAILED DESCRIPTION OF THE PREFERRED EMBODIMENTS

Hereinafter, a CNT composite and a preparation method of the same according to the embodiments of the present invention are explained in more detail.

According to one embodiment of the present invention, a CNT composite of which one or more functional groups represented by the following Chemical Formula 1 are bonded to the surface of a CNT may be provided.

[Chemical Formula 1]

In Chemical formula 1, n may be an integer of 1 to 10, $R_1$ and $R_6$ may independently be hydrogen or a $C_1$-$C_3$ alkyl, and $R_2$, $R_3$, $R_4$, and $R_5$ may independently be a $C_1$-$C_3$ alkyl or phenyl.

Through experiments, the present inventors confirmed that metal nanoparticles can be uniformly and highly densely decorated on the CNT, which may be prepared by the method disclosed below, without agglomerating, and the CNT composite having metal nanoparticles can have excellent electrical conductivity, and completed the present invention. Such CNT composite may have a form in which one or more functional groups are introduced to the surface of the CNT, and the part derived from the polysiloxane compound in Chemical Formula 1 acts to fix the metal nanoparticles uniformly. By applying the CNT composite, it is possible to prepare electronic materials that have excellent mechanical and electric properties, and the composite can be easily applied to various industrial fields. Particularly, the electronic materials to which the CNT composite is applied can be applied to the fields of isotropic conductive adhesives, solder joint technologies, and the like in the electronic package industry.

In Chemical Formula 1, the n may be an integer of 1 to 10, and preferably an integer of 5 to 10. When the n is over 10, the functional groups of Chemical Formula 1 may be tangled, and thus it may be difficult to fix the metal nanoparticles to the CNT composite.

The CNT can be obtained by a commonly known preparation method, and a method using arc discharge, a method of using a laser, a method of using carbon monoxide (CO) in the condition of high temperature and high pressure, a thermal chemical vapor deposition synthesis method, and the like can be exemplarily used. However, the CNT used in one embodiment of the present invention is not limited to what is prepared by the methods, and the CNT that is commonly used and obtained can be applied to the present invention without particular limitation.

Meanwhile, the CNT composite according to one embodiment of the present invention may further include a metal nanoparticle, and specific examples of the metal nanoparticle may be nanoparticle of palladium (Pd), rhodium (Rh), iridium (Ir), platinum (Pt), gold (Au), silver (Ag), or a mixture thereof, and preferably silver nanoparticles.

Meanwhile, the metal nanoparticle may be fixed to the CNT composite through a coordination interaction by the medium of the functional groups of Chemical Formula 1. The functional groups of Chemical Formula 1 may form particular sites on the CNT composite where the nanoparticles can be fixed regularly and uniformly, and the metal nanoparticles may be fixed to the composite through the coordination interaction by the medium of the functional groups. Thus, the metal nanoparticles may be bonded to the CNT composite with a uniform size and appropriate strength.

Meanwhile, according to another embodiment of the present invention, a method of preparing a CNT composite includes the steps of introducing an acylhalide group to the surface of CNT, and causing a reaction of the acylhalide group with a polysiloxane having amine groups so as to prepare a CNT composite of which the polysiloxane is bonded to the surface of the CNT by the medium of an amide group.

Through experiments, the present inventors confirmed that the CNT composite, of which the polysiloxane is bonded to the surface of the CNT by the medium of an amide group, is prepared by introducing an acylhalide group to surface of a CNT and reacting the acylhalide group with a polysiloxane having amine groups. Moreover, it is also confirmed that metal nanoparticles can be uniformly fixed to the CNT composite without agglomerating and the CNT composite having metal nanoparticles can have excellent electrical conductivity. Particularly, it is also recognized by the experiments that metal nanoparticles can be fixed more uniformly by applying a particular reaction condition during fixing of the metal nanoparticles to the CNT composite.

The step of introducing the acylhalide group may include the steps of treating the CNT with an acid, and causing a reaction of the acid-treated CNT with a halogenating agent.

The CNT can be used without particular limitation if it can be prepared by commonly known methods, and examples of such methods are as disclosed above. Furthermore, the acid treatment step of the CNT may be carried out in a solution including sulfuric acid, hydrochloric acid, nitric acid, and the like. The kinds of the acid, the concentration of the acid, and the conditions such as the reaction time, the reaction temperature, and the like are not particularly limited, and any commonly known method that can be applied to treat the CNT with an acid can be used without particular limitation.

Furthermore, thionyl chloride or phosphorus chloride, such as phosphorus dichloride, phosphorus trichloride, and phosphorus pentachloride, may be used as the halogenating agent.

Furthermore, the polysiloxane having amine groups may include the compound of the following Chemical Formula 2.

[Chemical Formula 2]

In the Chemical Formula 2, n may be an integer of 1 to 10, $R_1$ and $R_6$ may independently be hydrogen or a $C_1$-$C_3$ alkyl, and $R_2$, $R_3$, $R_4$, and $R_5$ may independently be a $C_1$-$C_3$ alkyl or phenyl. And preferably, $R_3$ and $R_4$ may independently be methyl or phenyl.

Furthermore, the polysiloxane having amine groups may include a polydimethylsiloxane, a polydiphenylsiloxane, a polymethylphenylsiloxane, or a mixture thereof.

Meanwhile, in another embodiment of the present invention, the method may further include the step of dispersing the CNT composite with ultrasonic waves in the presence of an organic solvent. Through experiments, it can be recognized that the CNT composites were agglomerated or tangled before the ultrasonic dispersion in the organic solvent, but the CNT composites were dispersed well after the ultrasonic dispersion. Therefore, the metal nanoparticles can be fixed more uniformly because the CNT composites are dispersed well through the ultrasonic dispersion process and the exposed surface area increases. A method and apparatus that are commonly used or known for dispersing and cleaning organic compounds can be used in the ultrasonic dispersion. Particularly, a commercial apparatus such as bar sonicator and the like can be used, but it is not limited to this. Furthermore, tetrahydrofuran (THF) can be used as the organic solvent, but it is not limited to this, and any known solvent that is commonly used for dispersing and cleaning organic compounds can be used without particular limitation.

Furthermore, another embodiment of the present invention may further include the step of curing the prepared CNT composite. Through the curing step, particular sites where the metal nanoparticles can be fixed with appropriate strength are formed on the CNT composite, and the metal nanoparticles can be fixed to the composite more easily and uniformly because the positions of the sites have uniform regularity and the size is also appropriately controlled.

Figure 9:
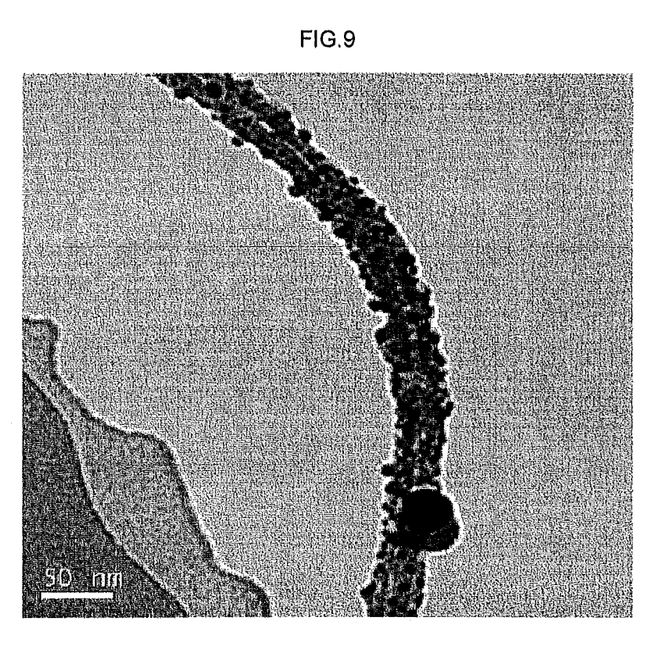
Figure 10:
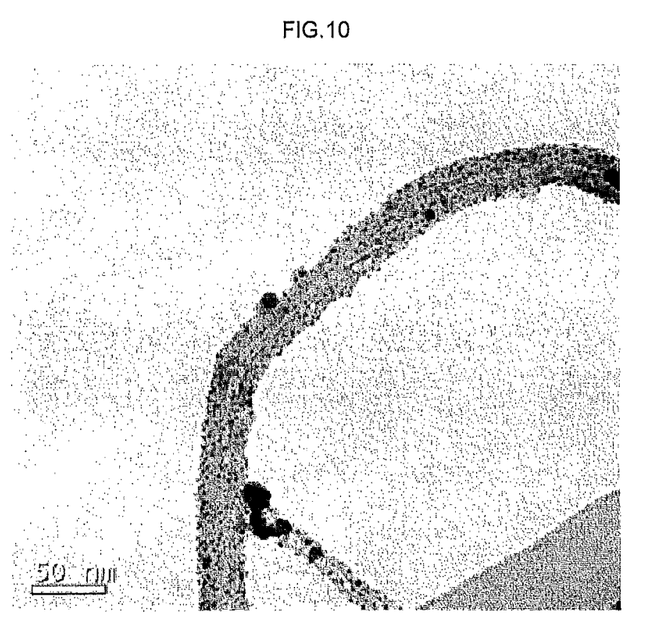

The curing step may be carried out at a temperature of 260 to 300° C. As shown in the example disclosed below, Comparative Examples 7 and 8, and FIGS. 9 and 10, when the curing temperature is lower than 260° C., the metal nanoparticles may not be fixed uniformly or may be agglomerated. Furthermore, when the curing temperature is higher than 300° C., the properties of the final product, the CNT composite, such as the electrical conductivity and the like, may be deteriorated.

Meanwhile, in another embodiment of the present invention, the method may further include the step of fixing a metal nanoparticle to the CNT composite. As disclosed above, the metal nanoparticle may include at least one nanoparticle of palladium (Pd), rhodium (Rh), iridium (Ir), platinum (Pt), gold (Au), or silver (Ag), and preferably silver nanoparticles.

The step of fixing the metal nanoparticle to the CNT composite may include the step of causing a reaction of the CNT composite in a precursor solution of the metal nanoparticle. If the CNT composite reacts in the precursor solution of the metal nanoparticle, the metal nanoparticle can be uniformly fixed to the CNT composite with appropriate strength through the coordination interaction bonding.

The precursor solution of the metal nanoparticle may include a nitrate, a sulfate, a chloride salt of said metals, and a silver nitrate solution can preferably be used.

Figure 5:
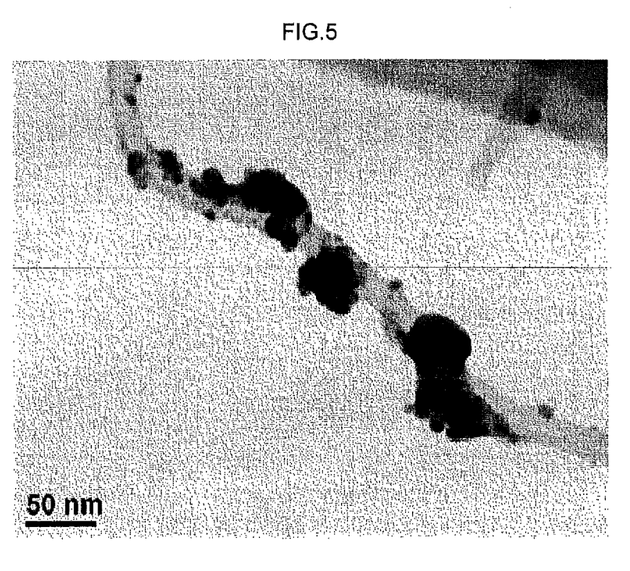
Figure 6:
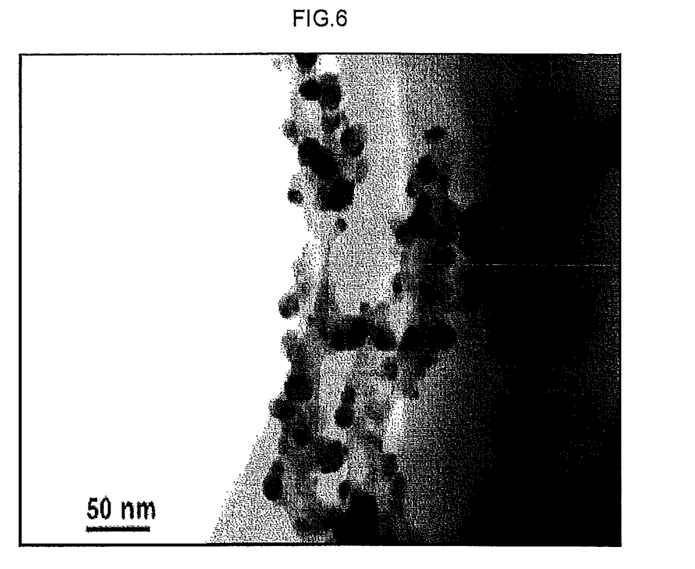
Figure 7:
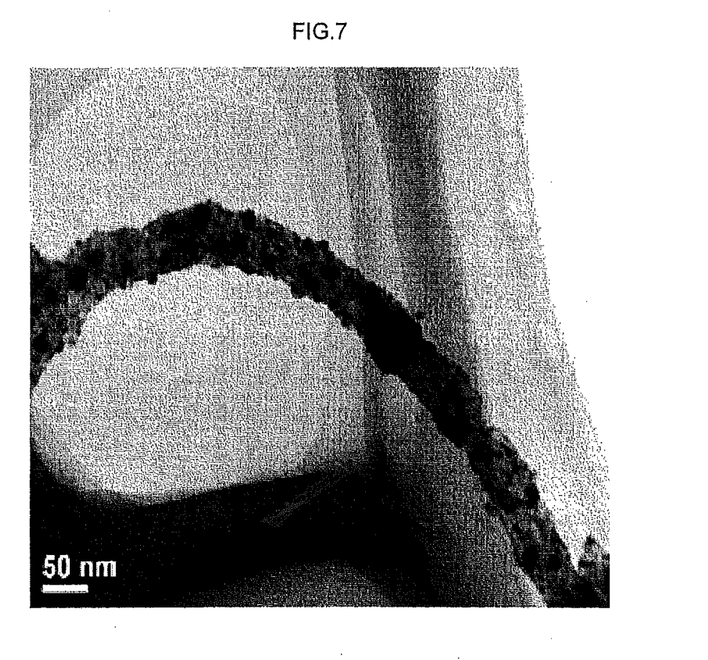
Figure 8:
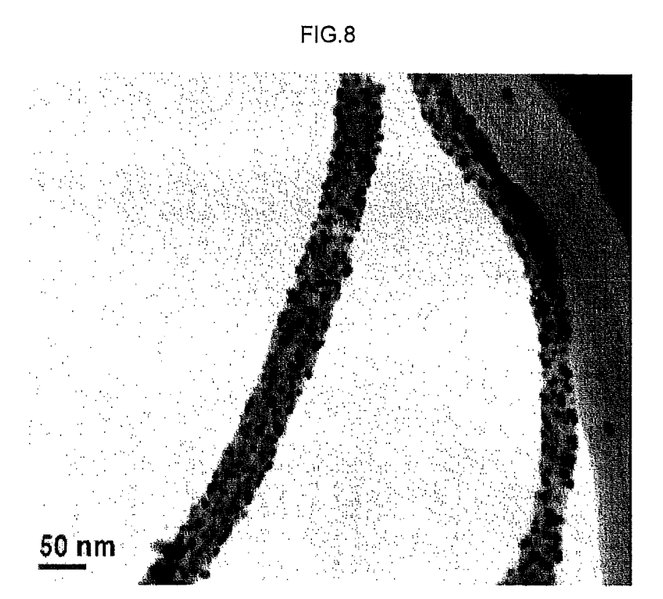

The precursor solution of the metal nanoparticle may have a concentration of 0.1 to 0.5M. When the concentration is lower than 0.1M, the amount of the metal nanoparticle fixed to the surface of the CNT composite may be insufficient, and when the concentration is higher than 0.5M, the metal nanoparticle may be agglomerated on the CNT composite or not uniformly fixed, and the electrical conductivity of the composite may deteriorate. Particularly, when the concentration is higher than 0.5M, the metal nanoparticle cannot be uniformly fixed as shown in Comparative Examples 3 and 4 disclosed below, and in FIGS. 5 and 6.

Figure 3:
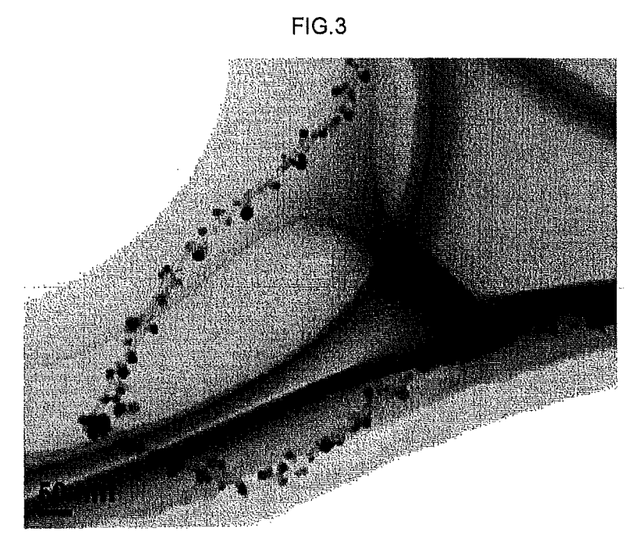
FIGS. 3 to 10 show TEM photographs showing the CNT composites of Comparative Examples 1 to 8 to which metal nanoparticles are fixed.
Figure 4:
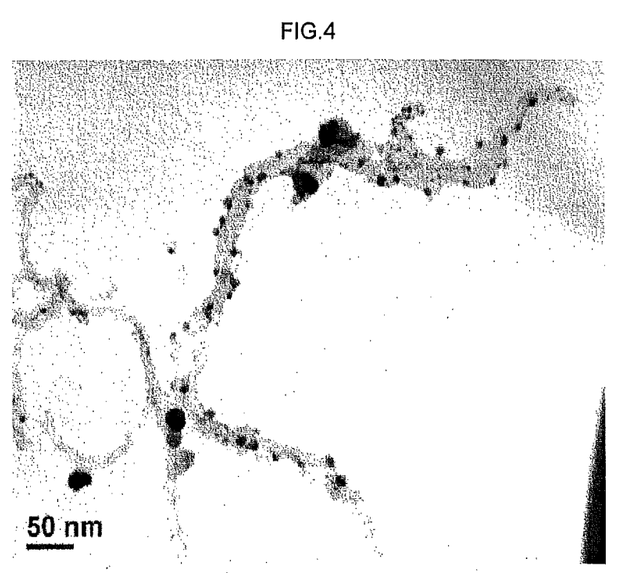

Furthermore, the step of fixing the metal nanoparticle may be carried out at a temperature of 130 to 150° C. If the temperature in the step of fixing the metal nanoparticle is too high or too low, the metal nanoparticle may be unevenly fixed to the composite, or the size of the fixed metal nanoparticles becomes irregular. Therefore, the electrical conductivity of the composite to which the metal nanoparticles are fixed at the temperature outside of the range may be largely deteriorated. As shown in Comparative Examples 1 and 2 disclosed below, and FIGS. 3 and 4, it can be recognized that the metal nanoparticle may not be fixed uniformly outside of the temperature of 130 to 150° C.

Furthermore, the step of fixing the metal nanoparticle may be carried out for 30 to 90 minutes. When the step of fixing the metal nanoparticle is carried out for less than 30 minutes, the amount of the metal nanoparticle fixed to the CNT may be insufficient, and when the time is over 90 minutes, the metal nanoparticle may be agglomerated on the CNT composite and the electrical conductivity of the composite may deteriorate.

According to the present invention, it is possible to fix the metal particles uniformly, and it is also possible to provide the CNT composite that has improved mechanical and electrical properties and can be applied to various industrial fields.

Hereinafter, functions and effects of the present invention are explained in more detail through concrete examples of the invention. However, the examples are provided only for exemplifying the present invention, and the scope of the present invention is not determined to or by this.

EXAMPLE

Preparation of the CNT to which the Metal Particle is Fixed

Acid Treatment on the CNT

The CNT (Hanwha Nanotech Co., Korea) was put in an 80° C. aqueous acid solution and reacted for 2 hours, wherein the aqueous acid solution was prepared by mixing sulfuric acid and nitric acid in a ratio of 3:1 and adding distilled water thereto so as to adjust the content of the acid to be 40%.

The acid-treated CNT was obtained by mixing the product of the above reaction with excess distilled water, and eliminating the solution including impurities by filtering the same. The processes of mixing with distilled water and filtering were repeated until the pH of the aqueous solution including the acid-treated CNT became about 7, and the acid-treated CNT was obtained by filtering the solution with a Teflon filter (pore size: 0.2 μm) and drying the product.

Acylation of the Acid-Treated CNT

The acid-treated CNT and an excess of thionyl chloride were refluxed in a 65° C. oil-bath for 24 hours. Then, the product was washed 4 times with tetrahydrofuran (THF) and filtered with the Teflon filter (pore size: 0.2 μm). The filtered product was sufficiently dried in an 80° C. oven for 24 hours, and a halogen acylated CNT (CNT-CO-Cl) powder was obtained.

Preparation of the CNT Composite

The halogen acylated CNT (CNT-CO-Cl) powder and polydimethylsiloxane (PDMS) having amine end groups (KF-8012, Shin-Etsu Chemical Co., Ltd., JAPAN/the equivalent of functional group 2200) were dispersed with ultrasonic waves in an ice bath by using a bar sonicator for 10 minutes. Then, the product of the ultrasonic dispersion was filtered, dispersed in THF solvent with ultrasonic waves for 2 minutes, and washed. The washed product was then filtered, dispersed in THF solvent with ultrasonic waves for 2 minutes, and washed again.

After finishing the washing process with THF, the CNT composite was cured at the curing temperature of 270° C. for 1 hour. The surface state of the CNT composite was observed by the field emission source scanning electron microscope and TEM photographs, and it was shown that the thickness of the polydimethylsiloxane having amine end groups was 1 to 5 nm.

Fixation of the Metal Particles to the CNT Composite 0.4M of silver nitrate was mixed with N-methyl-2-pyrrolidone (NMP) and dispersed with ultrasonic waves. The prepared CNT composite was put in said silver nitrate solution and dispersed with ultrasonic waves for 3 minutes, and then the nano-sized silver particles were fixed to the surface of the CNT composite with a reaction temperature of 140° C. and a reaction time of 1 hour.

Figure 1:
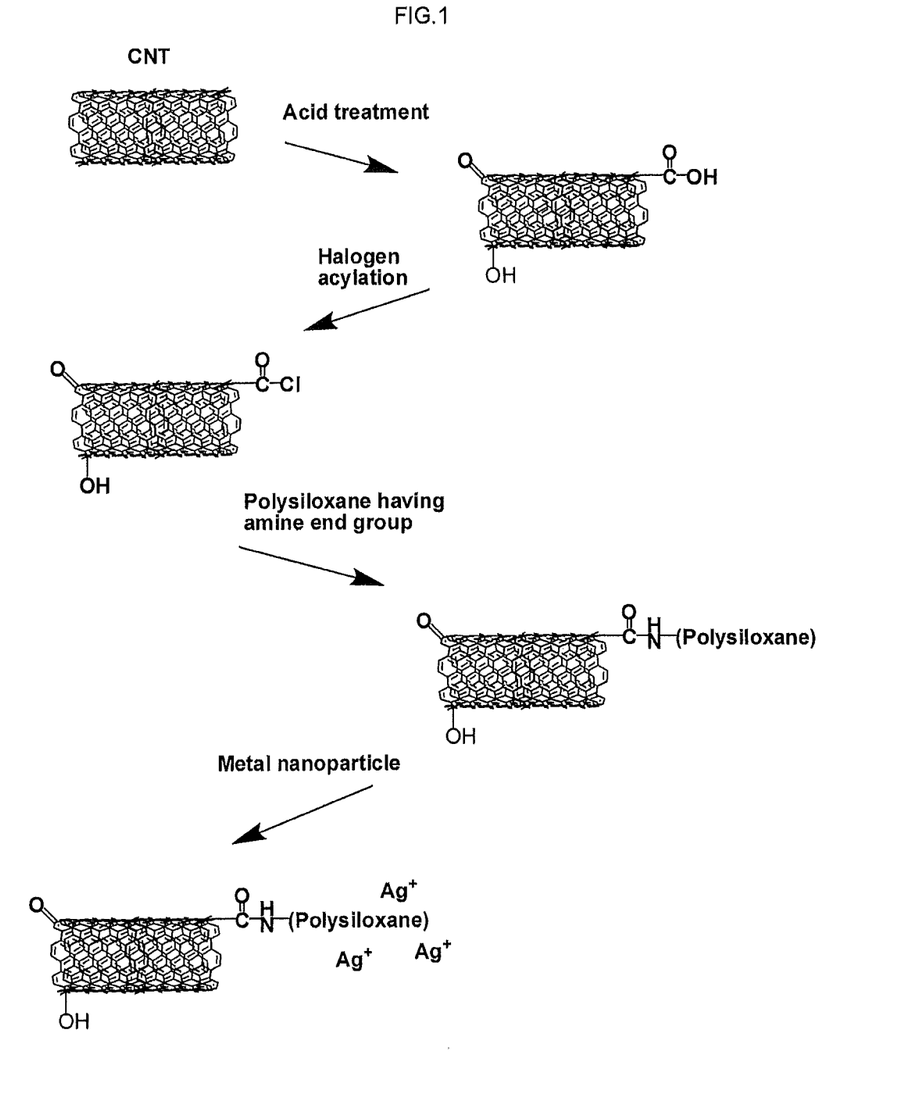
FIG. 1 shows a schematic process of the method of preparing the CNT composite to which metal particles are fixed.
Figure 2:
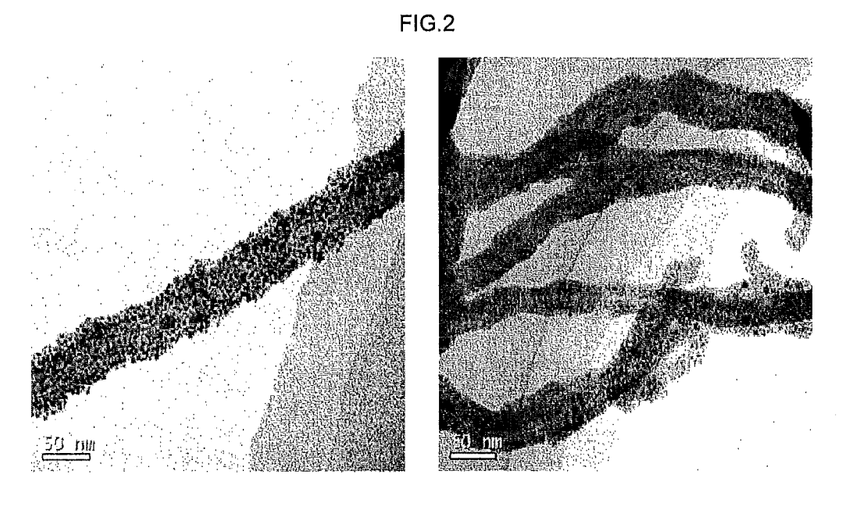
FIG. 2 shows transmission electron microscopy ("TEM") photographs showing the CNT composite to which silver nanoparticles are fixed.

After the reaction was finished, the CNT composite to which the silver nanoparticles were fixed was observed by using a TEM, and the results are shown in FIG. 2. Further, it is recognized in FIG. 2 that the silver particles are uniformly and densely fixed to the surface of the CNT composite.

COMPARATIVE EXAMPLES

Preparation of the CNT to which the Metal Particles are Fixed

Comparative Examples 1 to 8

In Comparative Examples 1 to 6, CNT composites to which the silver particles were fixed were prepared substantially according to the same method as in the example, except that the reaction temperature, the concentration of the silver nitrate, and the reaction time in the step of fixing the metal nanoparticles to the CNT were applied as disclosed in the following Table 1, and the curing process was omitted in the bonding step of the acylated CNT and the polysiloxane having amine end groups.

In Comparative Examples 7 and 8, the CNT composites to which the silver particles were fixed were prepared substantially according to the same method as in the example, except that the reaction temperature, the concentration of the silver nitrate, and the reaction time in the step of fixing the metal nanoparticles to the CNT, and the curing temperature in the bonding step of the acylated CNT and the polysiloxane having amine end groups were applied as disclosed in the following Table 1.

TABLE 1

Reaction Conditions in Example and Comparative Examples 1 to 8

| | Reaction Temperature (□) | Silver Nitrate Concentration (M) | Reaction Time (hr) | Curing Temperature (□) |
|---|---|---|---|---|
| Example | 140 | 0.4 | 1 | 270 |
| Comp. Example 1 | 120 | 0.4 | 1 | — |
| Comp. Example 2 | 160 | 0.4 | 1 | — |
| Comp. Example 3 | 140 | 0.6 | 1 | — |
| Comp. Example 4 | 140 | 0.8 | 1 | — |
| Comp. Example 5 | 140 | 0.4 | 2 | — |
| Comp. Example 6 | 140 | 0.4 | 3 | — |
| Comp. Example 7 | 140 | 0.4 | 1 | 230 |
| Comp. Example 8 | 140 | 0.4 | 1 | 250 |

The CNTs of Comparative Examples 1 to 8 to which metal particles were fixed were observed by a TEM, and the results are shown in FIGS. 3 to 10. From these results, it is recognized that the metal nanoparticles are fixed uniformly when the reaction temperature, the concentration of the silver nitrate, the reaction time in the step of fixing the metal nanoparticles to the CNT, the curing temperature in the bonding step of the acylated CNT, and the polysiloxane having amine end groups are controlled to be in a particular range.

Comparative Example 9

The metal nanoparticles were directly fixed to the acid-treated CNT substantially according to the same method as in the example, except that the acylation step and the step of reacting the CNT and the polydimethylsiloxane (PMDS) having amine end groups were omitted.

Experimental Examples

Measurement of Electric Conductivity

The metal nanoparticles-CNT composites prepared in the example and Comparative Example 9 were mixed with polydimethylsiloxane respectively according to the following Table 2, and coated on a polyethylene terephthalate (PET) film with the thickness of 0.8 μm by using a bar coater.

Further, the electrical conductivities of the coating layers were measured by using a 4-probe method(Loresta-GP, Mitsubishi Chemical Co., Japan).

TABLE 2

Results of the electrical conductivities

| | Example (S/cm) | Comparative Example 9 (S/cm) |
|---|---|---|
| CNT 1 wt % | $4.59 \times 10^{-7}$ | $1.94 \times 10^{-7}$ |
| CNT 2 wt % | $3.66 \times 10^{-3}$ | $3.75 \times 10^{-5}$ |
| CNT 3 wt % | $7.84 \times 10^{-2}$ | $1.01 \times 10^{-3}$ |

As shown in Table 2, it is recognized that the example in which the metal nanoparticles are fixed to the CNT composite prepared by applying the polysiloxane having amine end groups shows higher electrical conductivity than Comparative Example 9 in which the metal nanoparticles are fixed to the CNT that is only treated with an acid. It is also recognized that the increasing effect of the electrical conductivity becomes larger as the concentration of the CNT increases.

Therefore, the CNT composite of the example enlarges the increasing effect of the electrical conductivity, can have improved mechanical and electrical properties, and can be applied to various industrial fields, because it fixes the metal nanoparticles uniformly.

The invention claimed is:

1. A method of preparing a carbon nanotube composite, comprising:
   treating a surface of a carbon nanotube composite with an acid;
   introducing an acylhalide group to the acid-treated surface to cause a reaction of the acid-treated surface and the acylhalide group,
   wherein the acylhalide group is selected from the group consisting of thionyl chloride and phosphorus chloride;
   introducing a polysiloxane having amine end groups and at least one other functional group to the acylhalide group on the carbon nanotube composite to allow one of the amide end groups of the polysiloxane to bond to the acylhalide group on the surface of the carbon nanotube composite;
   curing the carbon nanotube composite at a temperature of 260 to 300° C.; and
   introducing a precursor solution of metal nanoparticles to the surface to cause a reaction between the metal nanoparticles and the at least one other functional group of the polysiloxane, thereby bonding the metal nanoparticles to the surface of the carbon nanotube composite via the at least one other functional group,
   wherein the precursor solution of metal nanoparticles is a silver nitrate solution, and
   wherein the polysiloxane includes a compound of the following Chemical Formula:

wherein, n is an integer of 1 to 10,
   $R_1$ and $R_6$ are independently hydrogen or a $C_1$-$C_3$ alkyl, and
   $R_2$, $R_3$, $R_4$, and $R_5$ are independently a $C_1$-$C_3$ alkyl or phenyl.

2. The method according to claim 1, wherein $R_3$ and $R_4$ are independently a methyl or a phenyl.

3. The method according to claim 1, further comprising dispersing the carbon nanotube composite with ultrasonic waves in the presence of an organic solvent.

4. The method according to claim 1, wherein the precursor solution of the metal nanoparticles has a concentration of 0.1 to 0.5M.

5. The method according to claim 1, wherein the bonding of the metal nanoparticles is carried out at a temperature of 130 to 150° C. for 30 to 90 minutes.

* * * * *